United States Patent [19]
Erickson

[11] Patent Number: 5,466,102
[45] Date of Patent: Nov. 14, 1995

[54] SYSTEM FOR COUPLING MACHINE TOOLS

[75] Inventor: Robert A. Erickson, Raleigh, N.C.

[73] Assignee: Kennametal Inc., Latrobe, Pa.

[21] Appl. No.: 168,802

[22] Filed: Dec. 16, 1993

[51] Int. Cl.$^6$ ............................................... B23B 31/103
[52] U.S. Cl. ...................... 409/232; 408/239 A; 409/234
[58] Field of Search .................................. 409/232, 233, 409/234; 82/160, 158; 408/239 A, 240; 279/141

[56] References Cited

U.S. PATENT DOCUMENTS

| | | | |
|---|---|---|---|
| 4,615,244 | 10/1986 | Reiter et al. | 82/160 |
| 4,709,454 | 12/1987 | Barnes | 24/590 |
| 4,715,753 | 12/1987 | Tack | 409/234 |
| 4,736,659 | 4/1988 | Erickson | 82/36 B |
| 4,740,122 | 4/1988 | Glaser | 409/232 |
| 4,784,542 | 11/1988 | Tack et al. | 409/234 |
| 4,836,068 | 6/1989 | Erickson | 82/160 |
| 5,143,495 | 9/1992 | Bosek | 409/233 |
| 5,186,476 | 2/1993 | Heel et al. | 409/234 X |
| 5,243,884 | 9/1993 | Haga et al. | 82/160 |
| 5,346,344 | 9/1994 | Kress et al. | 409/234 |

FOREIGN PATENT DOCUMENTS

| | | | |
|---|---|---|---|
| 0155539 | 9/1985 | European Pat. Off. . | |
| 0507147 | 10/1992 | European Pat. Off. . | |
| 0563979 | 10/1993 | European Pat. Off. . | |
| 2736412 | 3/1978 | Germany | 82/160 |

OTHER PUBLICATIONS

International Search Report mailed Mar. 28, 1995 for International Appln. PCT/US94/13217.
English Language Counterpart to EP 0507147 (5,346,344).
English Language Counterpart to EP 0155539 (U.S. Pat. No. 4,615,244).
German Standard DIN 69893 Part 1, Draft Aug. 1991, Hollow Taper Shanks for Automatic Tool Exchange, Type A Dimensions.
Tool–Spindle Connection System According to German DIN 69893 PT 2, By Brian Baker, Publication Data Unknown.
"The New Dimensions, MAPAL Clamping Chuck KS", High Precision Cutting Tool Systems, Publication Date Unknown.
"The Future of Toolholding," Standard Tool System, Valenite Corporation, 1992.

*Primary Examiner*—Daniel W. Howell
*Attorney, Agent, or Firm*—James G. Porcelli

[57] ABSTRACT

A coupling system (1) is provided for lockably coupling together machine tool components that comprises a male coupling (3) having a recess (19) at a distal end that includes follower surfaces (24), and female coupling (9) having an opening (31) disposed along its longitudinal axis for receiving the distal end of the male coupling (3), and a pair of opposing jaw members (12) pivotally mounted in the opening (31) and having cam surfaces (44) engagable with the follower surfaces (24) of the male coupling (3). The system (1) includes a drive train (13) for pivotally moving the jaw members (12) apart in order to interengage the cam (44) and follower surfaces (24) of the female (5) and male (3) couplings that includes an axially movable, ball-shaped element (52) disposed in opposing recesses (50) present in the jaw members (12) for prying the jaw members (12) apart, a pair of opposing wedge members (58) for moving the ball-shaped drive element (52) axially toward the free ends of the jaw members (12), and a screw (64) having right and left hand threads on either of its ends for moving the wedge members (58) toward and away from one another. The drive train (13) generates high clamping forces between the male (3) and female (5) couplings in a small envelope and with a large degree of mechanical advantage.

30 Claims, 4 Drawing Sheets

SYSTEM FOR COUPLING MACHINE TOOLS

BACKGROUND OF THE INVENTION

This invention generally relates to a system for coupling machine tools, and is specifically concerned with a system for detachably coupling machine tools to the toolholders of a modular tooling system by means of a small package having a high holding force that provides accurate and rigid tool couplings in all six degrees of freedom at both low and high rotational speeds.

Coupling systems for interconnecting machine tools are well known in the prior art. Such coupling systems include a hollow, frustro-conical male component that forms part of the tool which mates with a frustro-conical opening in a female component. The female component is typically part of a spindle for rotating the tool. The taper of both the frustro-conical components often has a slope of about 1 to 10 with respect to the longitudinal axis of the tool. Such a slope provides a rigid, on-center interference coupling when the components are pulled together by means of a clamping mechanism disposed in the interior of the female opening.

There are presently a variety of mechanisms for clamping together the frustro-conical male and female components of prior art coupling systems. In some of these mechanisms, the female component on the toolholder includes radially movable locking balls for engaging complementarily-shaped socket openings in the walls of the male component. When moved radially outwardly, the locking balls function to secure and pull in the frustro-conical tool shank into the frustro-conical opening in the toolholder. An axially slidable bolt having cam surfaces radially forces the locking balls outwardly into the socket openings. In other types of mechanisms, the female opening includes a radially expandable locking plunger which is extendable into the hollow interior of the frustro-conical male component. The locking plunger may include two or more radially movable fingers that engage openings in the wall of the frustro-conically shaped male component in order to forcefully wedge the male component of the tool into the female component of the toolholder.

While both of these general types of prior art coupling systems have shown themselves to be effective for their intended purpose, systems fabricated by different manufacturers are unfortunately not interchangeable with one another. Thus the end user of a tooling system has, up to recently, been forced to choose between one particular proprietary type of tooling and coupling system or another. To remedy this problem, the German government in 1987 standardized the dimensions of the envelope that such coupling systems were to have in a proclamation entitled "DIN 69890". However, this proclamation did not standardize the aspect ratio or type of coupling mechanism that was to clamp together the frustro-conical male and female coupling components. Specifications for a coupling system sufficiently standardized to permit interchangeability did not occur in Germany until the issuance of DIN 69893 in 1993 which sets forth the dimensions of the frustro-conical male component and female taper area that would secure the components together. This proclamation also specifies that the male component is to have an annular shoulder circumscribing its interior that defines a follower surface. By implication, the female component is to have a member with a cam surface that engages the male follower surface to lock the two components together. The standardized coupling system specified in DIN 69893 is already being manufactured by several German-based tooling companies, whose tooling systems are being sold to several of the major German automotive manufacturers. The growing implementation of DIN 69893 in Germany and elsewhere is likely to result in the adoption of these same specifications internationally.

DIN 69893 generally sets forth the dimensions and type of follower surfaces in the male component that are to be used to couple the components together. However, it does not specify the form that any cam members in the female component should take, or what drive mechanism is to be used to move these cam members into engagement with the follower surface within the male component, as different cam members and drive mechanisms can be used without impairing the interchangeability of coupling systems fabricated by different manufacturers. There presently exists a number of such cam designs and drive mechanisms. Unfortunately, there are a number of shortcomings associated with each.

For example, almost all prior art drive mechanisms employ an axially movable draw bar that expands the cam members by a camming action. While such draw bars may be used in applications where there are few if any axial space constraints (such as when the coupling system is used to connect a tool to the spindle of a machining center), they are difficult if not impossible to use in modular tooling systems where the overall size of the coupling envelope may not exceed a certain specified length. Still other shortcomings associated with draw bar type mechanisms is the fact that substantially all of the mechanical advantage used to generate the coupling force is derived from an axially oriented screw thread accessible only on the end of the tool, rather than on its side. The axial orientation of such screw threads makes access difficult in modular tooling systems where the tools are closely spaced, and impedes the operator's ability to change tools quickly. Additionally, the primary reliance upon a screw thread for the generation of mechanical advantage can lead to excessive wear between the screw threads and the threaded bore which receives it, which in turn can lead to inconsistent coupling forces over time.

Since the tensile force generated by the clamping mechanism causes the frustro-conical male and female coupling components which mate with an interference fit to tightly wedge together, some means must be provided for positively pulling or "bumping" these components apart when a change in tools is desired. To this end, many prior art plunger-type coupling systems include some sort of bumping mechanism. But, many of these mechanisms rely upon a spring to provide the necessary impulse to "bump" the male and female components apart. The use of springs not only complicates the coupling mechanism, but can result in an unreliable bumping action. While some of the aforementioned deficiencies of plunger-type clamping mechanisms could be overcome by the use of a locking ball mechanism, the use of locking balls requires the provision of holes through the tapered walls of the male component of the tool. Such holes are not allowed in the specification of DIN 69893.

Clearly, there is a need for a drive mechanism for radially expanding the cam members needed in DIN 69893 coupling systems which is sufficiently compact in the axial direction to be easily used in modular tooling systems. Ideally, the drive mechanism would afford an easily accessible radially-oriented actuator for the machine operator to facilitate quick tooling changes, and should be capable of applying large amounts of pull-back force between the frustro-conical male and female components with a high degree of mechanical advantage. Preferably, the drive mechanism should avoid the concentration of excessive pressures in any particular portion of its components which could result in excessive wear, shortened tool life, and inaccurate coupling forces between the male and female coupling members. Finally, the drive mechanism should provide a positive and reliable "bumping" action between the male and female components in order to effect quick tooling changes, and should be relatively easy and inexpensive to manufacture, and easy to assemble and disassemble and maintain.

SUMMARY OF THE INVENTION

Generally speaking, the invention is a coupling system that fulfills all of the aforementioned criteria without any of the shortcomings associated with the prior art. To this end, the invention is a coupling system for lockably coupling together a male coupling having a recess that includes follower surfaces, and a female coupling having an opening for receiving the male coupling, and a pair of opposing jaw members movably mounted in the opening having cam surfaces for engaging the follower surfaces of the male coupling when the jaw members are moved apart. The system comprises a drive train for forcefully moving the jaw members apart that includes an axially movable drive element that is preferably in the form of a ball disposed between the jaw members, and a pair of opposing wedge members for moving the drive element axially in a pinch-type mechanical action when the wedge members are moved toward one another. A screw member is provided which preferably includes both a right-handed and left-handed thread on either of its ends for driving the wedge members toward and away from one another in much the same fashion as a roller-skate clamp. The screw member includes a head having a hex socket that is radially accessible through an opening in a sidewall of the female coupling for effecting quick tool changes.

In addition to having wedging surfaces which axially move the ball-shaped drive element when the double threaded screw moves the wedge members toward one another, the wedge members further include surfaces for wedgingly prying apart the distal end of the male coupling from the opening within the female coupling when the screw member is turned to move the wedge members away from one another. Thus a simple positive "bump" action is provided without the need for springs or a complex and potentially unreliable configuration of mechanical elements.

The drive train of the coupling system advantageously provides three areas of mechanical advantage in addition to the pitch of the screw member that allow a system operator to quickly and conveniently generate large pull-back coupling forces between the male and female couplings. First, the angle of wedging engagement between the ball-shaped drive element and the opposing jaw members is such that the orthogonal movement of each of the jaw members is less than the axial movement of the drive element. Secondly, the angle of wedging engagement between the wedge members and the ball-shaped drive element is such that the axial movement of the drive element is greater than the orthogonal movement of either of the wedge members. Finally, because the ball-shaped drive element engages one end of the jaw members, and because the cam surfaces on the opposing jaw members are located between the ends of each of the jaw members, a portion of the length of each of the jaw members acts as a lever for forcefully inter-engaging the cam surfaces of the jaw members with the follower surfaces within the male coupling.

In the preferred embodiment, the drive element is a ball formed from bearing steel having a Rockwell hardness of between 58 and 60 C. Additionally, the engaging surfaces on both of the jaw members and the wedge members are cylindrical sections having a curvature complementary to the curvature of the ball-shaped drive element to provide, as a result of elastic deformation, a lenticularly shaped, surface-to-surface contact between these members and the drive element. Such surface-to-surface contact advantageously prevents point or line-shaped concentrations of force which could cause excessive wear in the elements of the drive train. Finally, the system includes a wedge support for counteracting the reactive force of the ball-shaped drive element on the screw member.

BRIEF DESCRIPTION OF THE SEVERAL FIGURES

Figure 3:
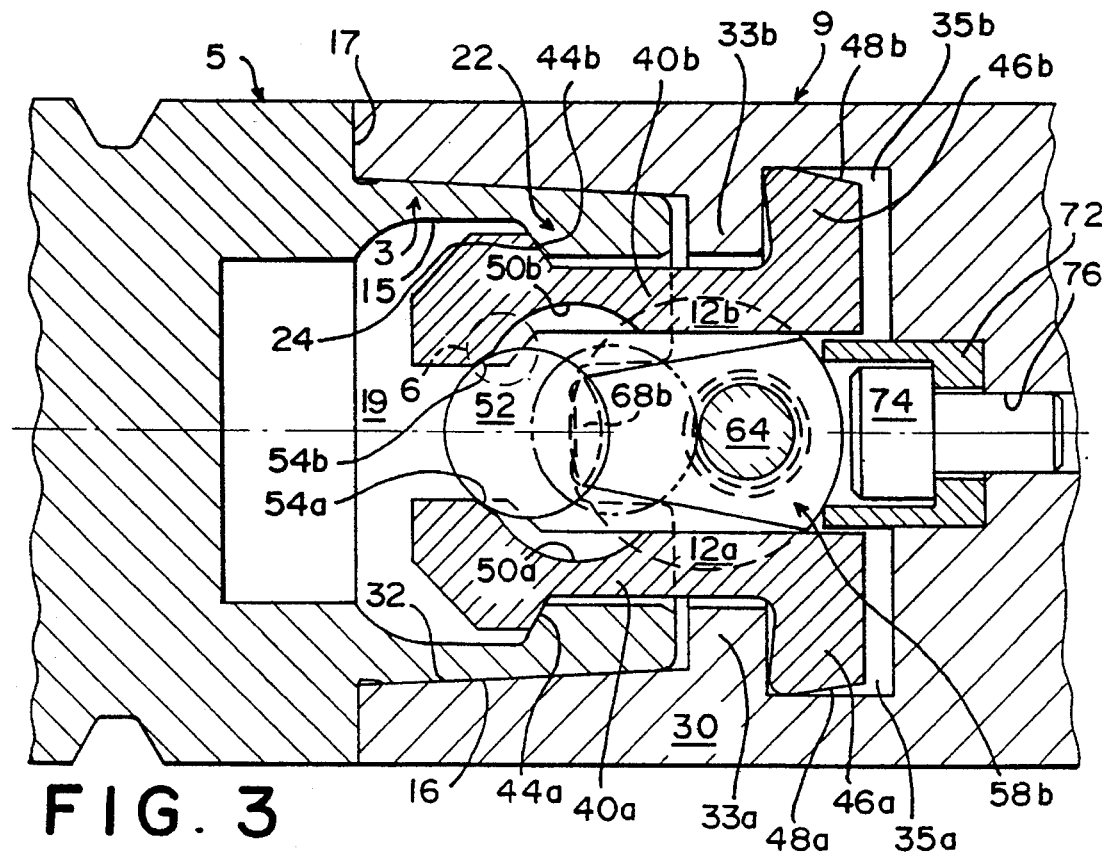
FIG. 3 is likewise a plan, cross-sectional view of the coupling system illustrated in FIG. 1 along the line 2,3—2,3 shown in assembled form, wherein the drive train has driven the drive ball into tight engagement with the inner surfaces of the jaw members in order to forcefully secure the mated male and female couplings together.
Figure 4:
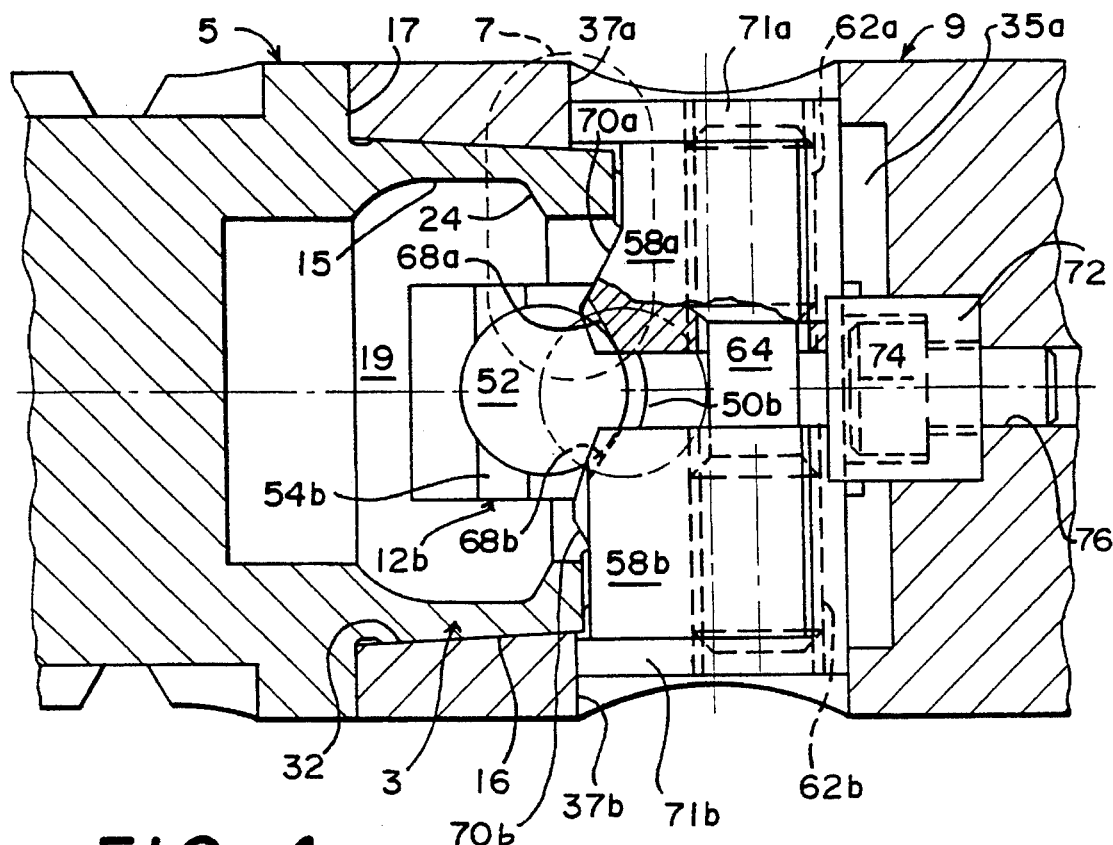
FIG. 4 is a cross-sectional side view of the coupling assembly illustrated in FIG. 1 along the line 4—4 as it would appear in assembled form.
Figure 7:
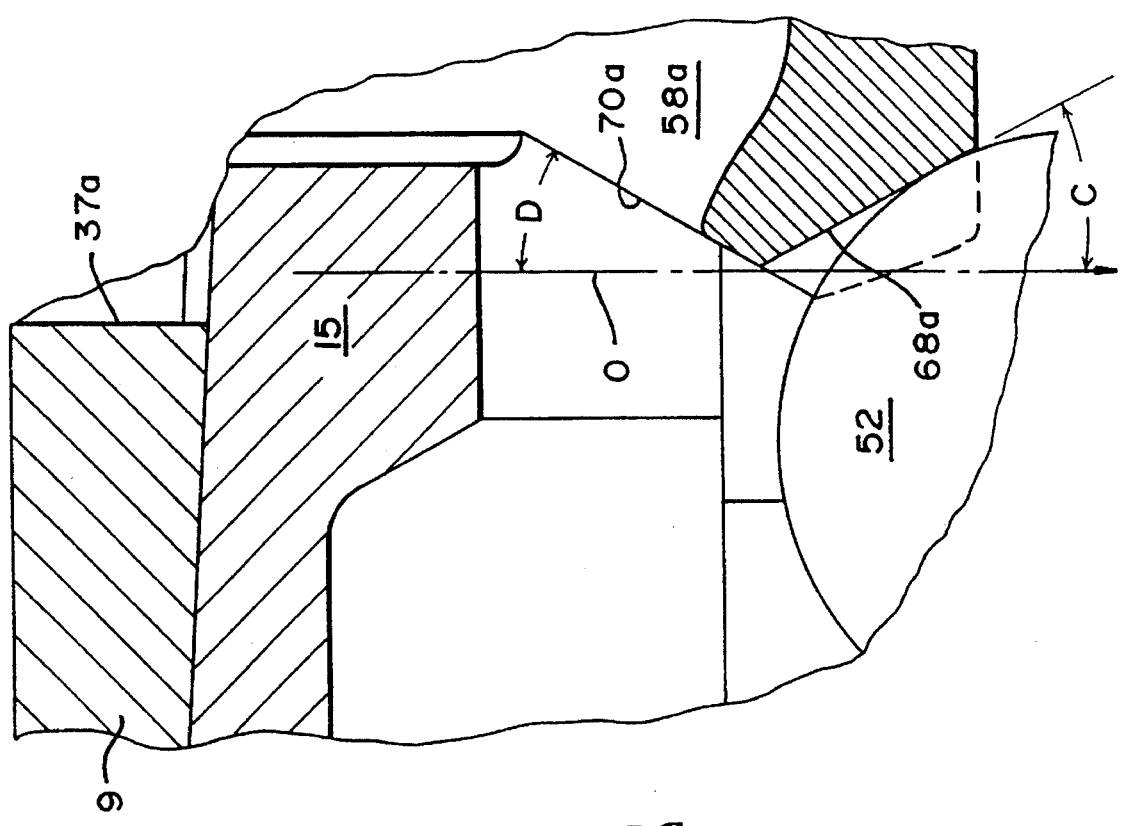
Figure 6:
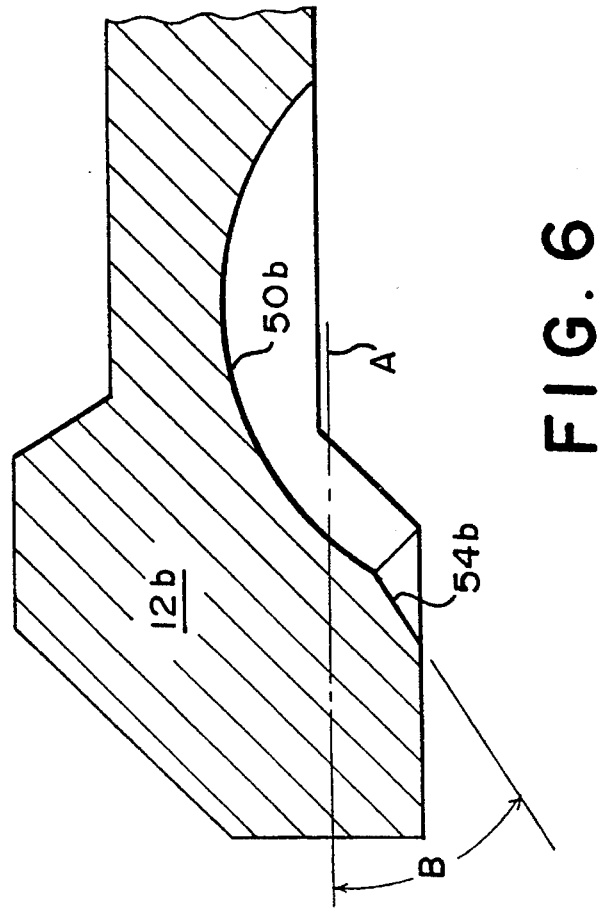

FIG. 6 is an enlarged view of the area surrounded by the dotted circle 6 of FIG. 3 illustrating the angle of engagement between the drive ball and the engagement surface 54b, and FIG. 7 is an enlarged view of the area surrounded by the dotted oval 7 illustrated in FIG. 4 demonstrating the angle of engagement between the drive ball and the inner wedge surface 68a and the outer bump surface 70a.

DETAILED DESCRIPTION OF THE SEVERAL FIGURES

Figure 1:
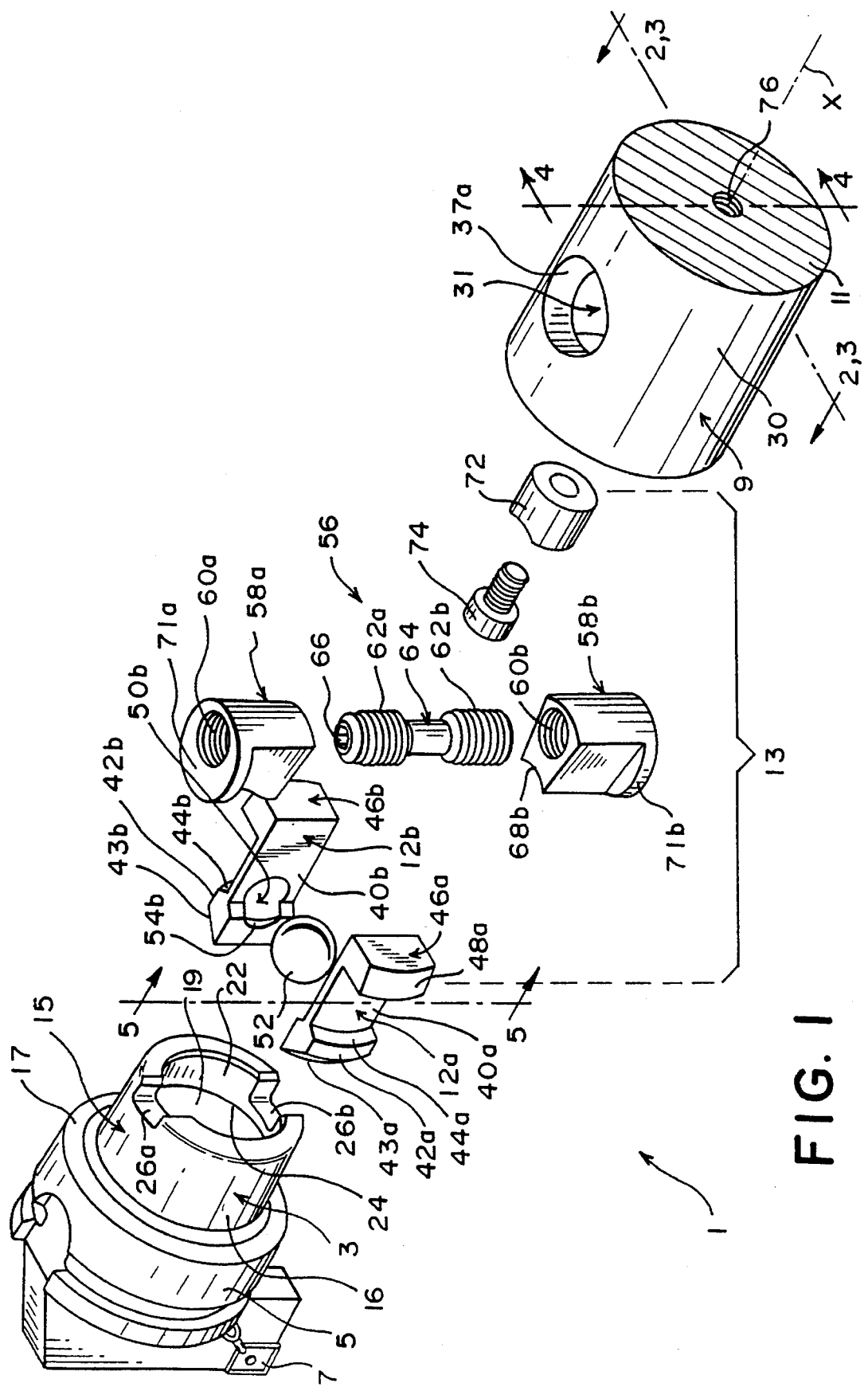
FIG. 1 is an exploded perspective view of the coupling system of the invention.

With reference to FIG. 1 wherein like numbers designate like components throughout all the several figures, the coupling system 1 of the invention comprises a male coupling 3 which is part of a tool body 5 which may, for example, hold an insert 7 of the type used to machine metal. The system 1 further includes a female coupling 9 which is part of a toolholder 11 which may be, for example, a spindle for turning the tool body 5 attached to the male coupling 3. In certain operations, both the male and female couplings 3,9 may rotate around an axis of rotation to machine a static workpiece. However, in other operations the male and female coupling 3,9 may be static and the workpiece may rotate. As will be described in more detail later, the female coupling 9 is substantially hollow, and houses a pair of opposing jaw members 12a,b. These jaw members 12a,b are radially expandable by means of a drive train 13, and forcefully mate and interlock the male and female couplings 3,9 of the system 1.

Figure 2:
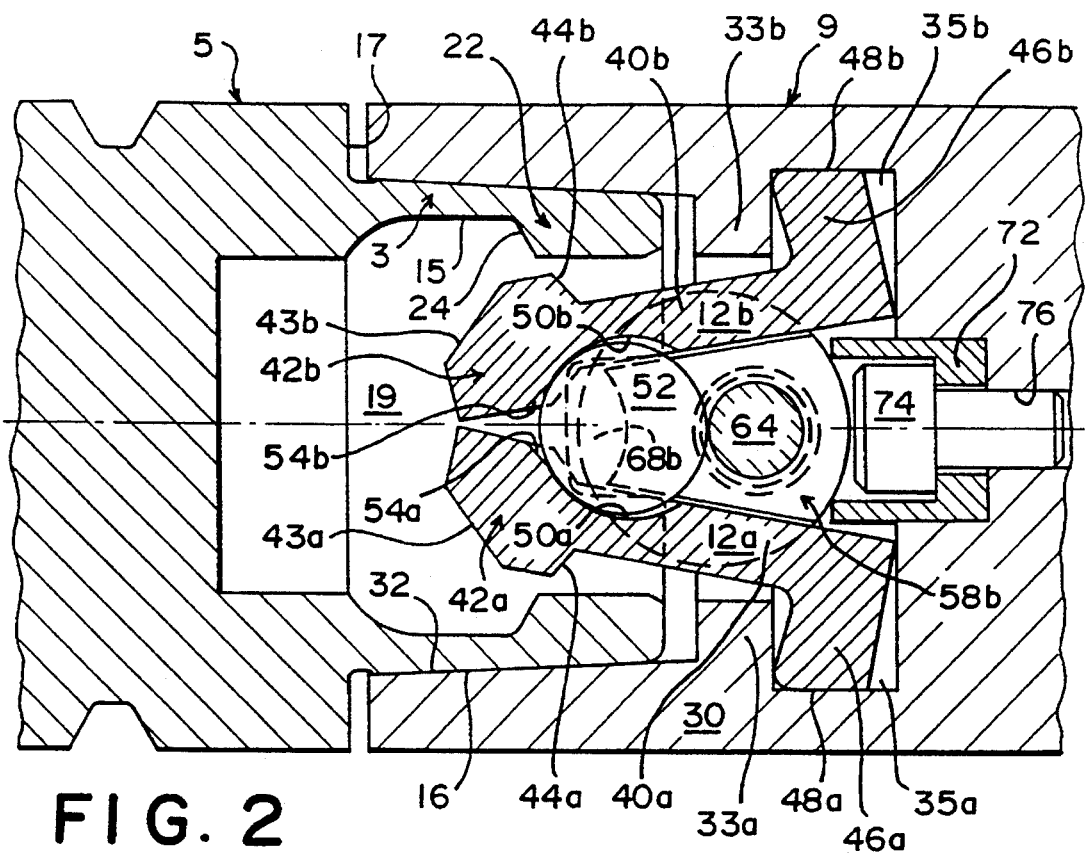
FIG. 2 is a plan cross-sectional view of the coupling system of FIG. 1 along the line 2,3—2,3 as it would appear in assembled form with the drive ball in an undriven state between the jaw members in order to facilitate the mating of the male and female coupling of the system.

As shown in FIGS. 2 and 3, the male coupling 3 includes a hollow shank 15 having a frustro-conical outer surface 16 which is preferably tapered at a slope of approximately 1 to 10 with respect to the longitudinal axis of the male and female couplings 3 and 9. The proximal end of the frustro-conical shank 15 is integrally connected to the tool body 5 as shown. An annular coupling face 17 circumscribes the junction between the shank 15 and the tool body 5. The shank 15 is ring-shaped, and encloses a frustro-conical interior 19. The distal inner end of the shank 15 is circumscribed by an annular shoulder 22 that defines, on its rear face, a frustro-conical follower surface 24. As is best seen in FIG. 1, the distal end of the shank 15 also includes a pair of opposing alignment slots 26a,b for properly aligning the male coupling 3 within the interior of the female coupling 9 incident to the coupling operation.

With reference now to FIGS. 3 and 4, the female coupling 9 has a generally cylindrical body 30 with a hollow interior 31 (see FIG. 1) defined by a frustro-conical inner wall 32 that is complementary in shape to the outer surface 16 of the shank 15 of the male member 3. A pair of opposing, arcuate lugs 33a,b partially circumscribes the inner wall 32 of the cylindrical body 30 near its proximal end. These arcuate lugs 33a,b define a pair of opposing recesses 35a,b at the proximal end of the interior 31. As is best seen in FIGS. 1 and 4, the cylindrical body 30 of the female coupling 9 also has a pair of opposing, circular openings 37a,b (37b not shown) toward its proximal end for a purpose which will become clear shortly.

Figure 5:
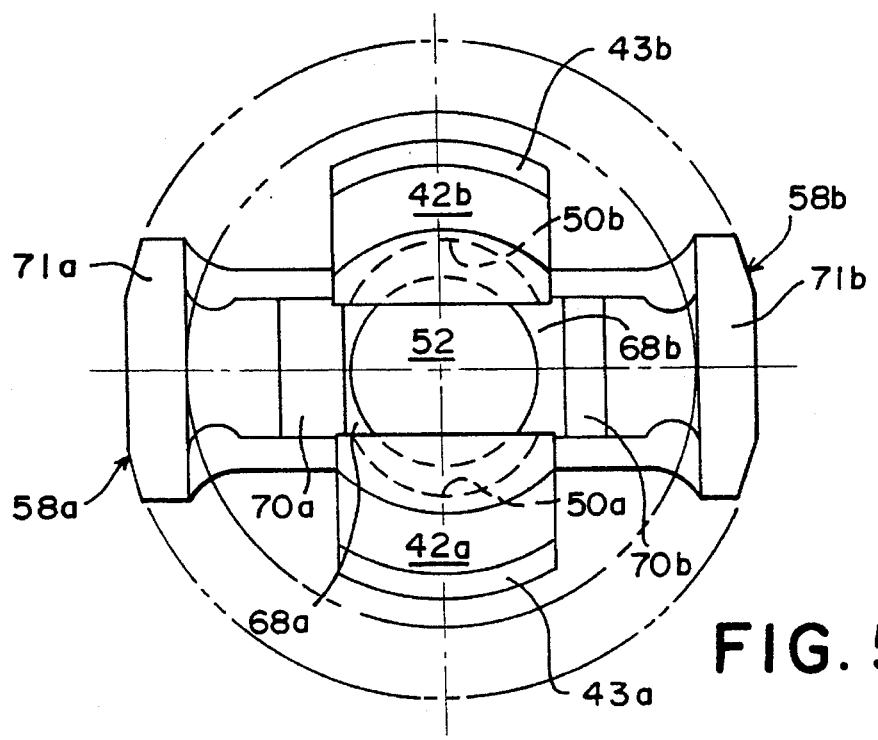
FIG. 5 is an end view of only the jaw members, the drive ball, and the ball driver assembly along the line 5—5 of FIG. 1 as they would appear in assembled form and rotated 90° counterclockwise.

With reference now to FIGS. 1, 3, and 5, the jaw members 12a,b each include an elongated body portion 40a,b. Note the view in FIG. 5 has been rotated 90° counterclockwise. The distal end of each body portion 40a,b includes an arcuate ledge 42a,b. Each of these ledges includes a tapered lead-in surface 43a,b for facilitating the insertion of the jaws in the non-expanded state illustrated in FIG. 2 into the hollow interior 19 of the male coupling 3. Each of these ledges 42a,b further includes a cam surface 44a,b which is complementary in shape to the frustro-conical follower surface 24 of the annular shoulder 22 that circumscribes the interior of the male coupling 3. The proximal end of each of the elongated body portions 40a,b of the jaw members 12a,b includes a foot 46a,b having a tapered side 48a,b. The foot 46a,b of each of the jaw members 12a,b is insertable into the recesses 35a,b and pivotally movable on the proximal surface of each of the arcuate lugs 33a,b. The tapered sides 48a,b of each foot 46a,b allows the feet to pivot without interference with the inner surface of the female coupling 9. On the inner surface of each of the jaw members 12a,b a concave recess 50a,b is provided as shown.

With reference now to FIGS. 1, 2, and 3, the drive train 13 of the system 1 generally comprises a drive ball 52 captured within the opposing concave recesses 50a,b of the jaw members 12a,b, and a ball driver assembly 56 for forcefully moving the ball 52 from the position illustrated in FIG. 2 to the position in FIG. 3. In the preferred embodiment, the drive ball 52 is formed from polished bearing steel having a Rockwell hardness of between about 58 to 60 C. In addition to having concave recesses 50a,b for captively housing the drive ball 52 when it is in the position illustrated in FIG. 2, each of the jaw members 12a,b further includes an engagement surface 54a,b disposed at the proximal ends of the concave recesses 50a,b for receiving the drive ball when the ball driver assembly 56 pushes it into the position illustrated in FIG. 3. The contour of each of the engagement surfaces 54a,b is cylindrical such that lenticular-shaped contact is made between the surface of the drive ball 52, and the engagement surfaces 54a,b due to elastic deformation between these components.

The ball driver assembly 56 is formed from a pair of opposing wedge members 58a,b, each of which includes threaded bores 60a,b for receiving the threaded, opposing ends 62a,b of a double threaded screw 64. The upper end 62a of the screw 64 (shown in FIG. 1) includes a hex socket 66 for receiving the end of an allen wrench (not shown). The pitch of the threads on the opposing ends 62a,b are oppositely-handed, as are the threads of the bore 60a,b of the wedge members 58a,b. The opposite-handedness of these threads causes the wedge members 58a,b to move inwardly toward one another, or outwardly away from one another when an allen wrench is used to turn the double threaded screw 64 in one direction or the other in "skate clamp" fashion.

As is best seen in FIGS. 4, 5, and 7, each of the wedge members 58a,b includes an inner wedge surface 68a,b for engaging and wedgingly pushing the drive ball 52 toward the distal ends of the jaw members 12a,b when the wedge members 58a,b are drawn inwardly by the double threaded screw 64. Outer bump surfaces 70a,b are also provided on each of the wedge members 58a,b to pry the outer end of the male coupling 3 from the female coupling 9 when the wedge members are drawn outwardly by double-threaded screw 64. Finally, each of the wedge members 58a,b includes a circular cap member 71a,b at its outer end that is slidably movable within the opposing circular openings 37a,b in the cylindrical body 30 of the female coupling 9.

Disposed between the central portion of the double threaded screw 64 and the bottom of the hollow interior 31 of the female coupling 9 is a support pedestal 72. Pedestal 72 is secured into position by means of a mounting screw 74 screwed into a threaded bore 76 as shown, and functions to support the wedge members 58a,b against the reactive forces applied against it by the drive ball 52.

The operation of the coupling system 1 may best be understood with respect to FIGS. 2, 3, 6, and 7. Initially, the wedge members 58a,b are screwed apart into a position to where only the inner edges of the inner wedge surfaces 68a,b come in contact with the drive ball 52. When the wedge members 58a,b are so positioned, the drive ball 52 is loosely captured between the opposing concave recesses 50a,b located in the inner surfaces of the jaw members 12a,b. When the drive ball 52 is so positioned, the distal ends of the jaw members can pivot radially inwardly into the position illustrated in FIG. 2, which allows the jaw members 12a,b to be easily inserted into the interior 19 of the male coupling 3 with the help of the tapered lead-in surfaces 43a,b. The system operator then proceeds to manually push the male and female couplings 3,9 with the alignment slots 26a,b aligned with the double-threaded screw 64 until the cam surfaces 44a,b of the jaw members 12a,b overlie the follower surface 24 that circumscribes shoulder 22. In the next step of the coupling operation, the system operator turns the double threaded screw 64 by means of a hex wrench (not shown) inserted into the socket 66 of the screw 64 in a direction which causes the wedge members 58a,b to move toward one another. Because the inner wedge surfaces 68 are canted at an angle C which is 30° from a line O orthogonal to the longitudinal axis A, a mechanical advantage is realized between the drive ball 52 and each of the inner wedge surfaces 68a,b. Specifically, for every millimeter that the wedge members 58a,b are moved along the orthogonal line O, the drive ball 52 moves only 0.58 millimeters, thereby resulting in a 1.7 to 1 mechanical advantage.

As the drive ball 52 is forcefully moved toward the distal ends of the jaw member 12a,b by the wedge members 58a,b, the drive ball 52 rolls out of the concave recesses 50a,b and into the engagement surfaces 54a,b best seen in FIG. 6. Because the curvature of engagement surfaces 54a,b is complementary in shape to the curvature of the spherical surface of the drive ball 52, the ball 52 again advantageously makes a lenticular-shaped area contact due to elastic deformation with these surfaces as it is driven forward. Since each of the rounded engagement surfaces 54a,b is canted in an angle B approximately 30° with respect to a line A parallel to the axis of rotation of the male and female couplings 3,9, another 2 to 1 mechanical advantage is realized. In other words, for every millimeter that the drive ball 52 travels along the line A, the distal ends of the jaw members 12a,b are swung only 0.58 millimeters radially outwardly. When the drive ball finally arrives at the position illustrated in FIG. 3, the cam surfaces 44a,b on the end of the jaw members 12a,b have wedgingly engaged the frustro-conical follower surface 24 on the annular shoulder 22 of the male coupling 3 to such an extent that the outer surface 16 of the male shank 15 has been firmly pulled into engagement with the inner wall 32 of the female coupling 9, and the distal end of the cylindrical body 30 of the female coupling 9 has come into engagement with the annular coupling face 17 circumscribing the male coupling 3. Thus positioned, a firm and secure coupling has been achieved between the male and female couplings 3 and 9. In addition to the mechanical advantages provided by the pitch of the double threaded screw 64 in pulling the wedge members 58a,b inwardly, and the 1.7 to 1 mechanical advantages provided between the drive ball 52 and the inner wedge surfaces 68a,b and the engagement surfaces 54a,b of the jaw members 12a,b (which amounts to a 4 to 1 mechanical advantage overall between these components) there is a further advantageous component of leverage that occurs between the drive ball 52 and the elongated body portions 40a,b of the jaw members 12a,b. Specifically, as can best be appreciated with respect to FIG. 3, because the engagement surfaces 54a,b on the jaw members 12a,b distally extend beyond the cam surfaces 44a,b of these members, there is a significant amount of leverage between the drive ball 52 and the distal ends of the jaw members 12a,b as the ball 52 radially expands the jaw members 12a,b into the position illustrated in FIG. 3. The sum total of all of the mechanical advantages afforded between the drive ball 52, the double threaded screw 64, the wedge members 58a,b, and the jaw members 12a,b, allows the system 1 to generate extremely large coupling forces between the male and female couplings 3 and 9 in a very compact package.

To disengage the male and female couplings 3 and 9, the screw 64 is turned in the opposite direction to forcefully draw the wedge members 58a,b apart. The drive ball 52 retreats back into the concave recesses 50a,b, and the outer bump surfaces 70a,b then wedgingly engage the outer edge of the male component 3. This wedging action forcefully and reliably pries the male component 3 out of the frustro-conical interior of the female component 9.

The configuration of the various components of the system 1 allows it to be very easily and conveniently assembled, as may be appreciated with reference to FIG. 1. In the first step of assembly, the support pedestal 72 is installed by means of a mounting screw 74. Next, each foot 46a,b of each of the jaw members 12a,b is hung over its respective arcuate lug 33a,b disposed in the interior 31 of the female coupling 9. Next, the drive ball 52 is dropped through one of the circular openings 37a,b and seated between the concave recesses 50a,b of the opposing draw members 12a,b. One end 62a of the double threaded screw 64 is then threaded a couple of turns into the threaded bore 60a of one of the wedge members 58a. The free end of the double threaded screw 64 is next inserted through one of the opposing circular openings 37a,b. In this position, the threaded bore 60b of the other wedge member 58b is screwed into the free end of the double threaded screw 64. The double threaded screw 64 is then turned until the cap portion 71a,b of each of the wedge member 58a,b are flush with the exterior surface of the female coupling 9.

While the coupling system 1 of the invention has been described with respect to a preferred embodiment, various modifications, variations, and additions will become evident to persons of ordinary skill in the art. Also such variations, modifications, and additions are intended to fall within the scope of this invention, which is limited only by the claims appended hereto.

What is claimed is:

1. A coupling system for lockably coupling together machine tool components, comprising:
   (a) a male coupling having a recess at a distal end that includes follower surfaces;
   (b) a female coupling comprised of:
      (i) a body having an axis,
      (ii) an opening disposed along said axis for receiving the distal end of said male coupling and having walls,
      (iii) a plurality of lugs within said opening extending from said walls, and
      (iv) a plurality of opposing jaw members movably mounted in said opening and having feet which engage said lugs to limit axial travel of said members and said jaw members further having cam surfaces for engaging said follower surfaces and urging said surfaces both radially outwardly from said axis and longitudinally along said axis when said jaw members are moved apart orthogonally with respect to said axis to mate said male and female couplings together, and
   (c) a drive train for moving said jaw members apart, including:
      (i) an axially movable drive element for driving said jaw members apart,
      (ii) a pair of opposing wedge members orthogonally movable with respect to said axis for moving said drive element axially, and
      (iii) a screw member for driving said wedge members orthogonally with respect to said axis toward and away from one another.

2. A coupling system as defined in claim 1, wherein said wedge members further wedgingly engage and drive apart the distal end of the male coupling from the opening of the female coupling when said screw member drives the wedge members orthogonally away from one another.

3. A coupling system as defined in claim 1, wherein the angle of wedging contact between the drive element and the jaw members is such that the distance that each of the jaw members moves orthogonally with respect to said axis is less than the axial distance traveled by the drive element whereby a mechanical advantage is obtained between the drive element and the jaw members.

4. A coupling system as defined in claim 1, wherein the angle of wedging contact between the wedge members and the drive element is such that the distance that each of the wedge elements moves orthogonally is less than the distance that the drive element travels axially whereby a mechanical advantage is obtained between the pair of wedge members and the drive element.

5. A coupling system as defined in claim 1, wherein the jaw members are pivotally mounted on one end to the female coupling, and the drive element engages the jaw members at a point on an opposite end of each which is further away from said one end of each than said cam surfaces to provide a mechanical advantage between the action of the drive element driving apart the jaw members and the inter-engagement between the cam and follower surfaces of the jaw members and the male coupling, respectively.

6. A coupling system as defined in claim 1, wherein the screw member is orthogonally oriented with respect to said axis and includes a screw head accessible from a sidewall of the female coupling.

7. A coupling system as defined in claim 6, wherein the screw member includes right and left hand threads engaged to different ones of said jaw members, respectively.

8. A coupling system as defined in claim 1, wherein the drive element is free floating in a space created by opposing recesses in said jaw members.

9. A coupling system as defined in claim 7, wherein said drive element is a ball.

10. A coupling system as defined in claim 9, wherein said jaw members and said wedge members each include cylindrical wedge surfaces which are substantially complementary in curvature to the spherical outer surface of said ball to provide lenticular type surface contact between said ball and said jaw members and wedge members.

11. A coupling system for lockably coupling together machine tool components comprising:
   (a) a male coupling having a cylindrical distal end including a recess that includes follower surfaces;
   (b) a female coupling having
      (i) a body with a cylindrical opening defining walls for receiving the distal end of the male coupling, said cylindrical opening having walls with a pair of lugs within said opening extending from said walls, and
      (ii) a pair of opposing jaw members movably mounted within said opening including feet which engage said lugs to limit axial travel of said members and further including cam surfaces for engaging said follower surfaces and urging said surfaces both radially outwardly from said axis and longitudinally along said axis when said jaw members are radially moved apart to mate said male and female couplings, and
   (c) a drive train for radially moving said jaw members apart, including
      (i) a free floating drive element movable along the axis of rotation of said cylindrical opening and disposed between said jaw members for driving said jaw members apart,
      (ii) a pair of opposing wedge members for axially moving said drive element when moved radially toward one another, and
      (iii) a radially-oriented screw member for driving said wedge members radially toward and away from one another.

12. A coupling system as defined in claim 11, wherein said jaw members each have one end pivotally mounted within said openings and an opposite end that includes said cam surfaces, and wherein said free floating drive element functions to pivotally move the opposite ends of said jaw members apart from one another.

13. A coupling system as defined in claim 11, further comprising a support pedestal disposed between said screw member and a bottom wall defining said cylindrical opening of said female couple for counteracting the reactive shear forces that said drive element applies to said wedge members.

14. A coupling system as defined in claim 11, wherein said free floating drive element is a ball.

15. A coupling system as defined in claim 14, wherein each of said jaw members and said wedge members includes wedge surfaces that are substantially complementary in curvature to the outer surface of said ball for achieving an area-type, lenticular contact between said ball and said jaw and wedge members due to elastic deformation.

16. A coupling system as defined in claim 14, wherein said ball is made from bearing steel having a hardness of between 58 to 60 Rockwell C.

17. A coupling system as defined in claim 11, wherein said female coupling has outer sidewalls including opposing openings for receiving said wedge members during the assembly of said system, and for affording access to said screw member.

18. A coupling system as defined in claim 17, wherein one of said sidewall openings provides a passageway for the installation of said free floating drive element between said jaw members during the assembly of the coupling system.

19. A coupling system as defined in claim 11, wherein each of said wedge members includes wedge surfaces for engaging and driving apart the distal end of the male coupling from the recess of the female coupling when said screw member drives the wedge members away from one another.

20. A coupling system as defined in claim 11, wherein said screw member is radially disposed with respect to sidewalls of said female coupling, and includes a screw head for affording radial access to said screw member, and right and left handed threads engaging each of said wedge members, respectively.

21. A coupling system for lockably coupling together machine tool components, comprising:
   (a) a male coupling having a cylindrical distal end including a recess that includes follower surfaces;
   (b) a female coupling having a cylindrical opening for receiving the distal end of the male coupling, and a pair of opposing jaw members having one end pivotally mounted within said recess and opposite ends including cam surfaces for engaging said follower surfaces when said jaw members are pivotally moved apart in order to mate said male and female couplings, and
   (c) a drive train for pivotally moving said jaw members apart, including a ball disposed between said jaw members for wedgingly spreading said jaw members apart when moved along the axis of rotation toward opposite ends of said jaw members, a pair of opposing wedge members for wedgingly moving said ball axially when moved radially toward one another, and for wedgingly engaging and driving apart the distal end of the male coupling from the opening in the female coupling when said screw member drives the wedge members away from one another, and a screw member for driving said wedge members radially toward and away from one another,
   wherein the radial movement of each of said jaw members is less than the axial movement of said ball which in turn is less than the radial movement of said wedge members in order to provide a mechanical advantage between said wedge members, said ball, and said jaw members.

22. A coupling system as defined in claim 21, wherein the ball engages the jaw members at a point on an end opposite from said pivotally mounted end which is further away from said pivotally mounted end than said cam surfaces to provide a mechanical advantage between the action of the drive element driving apart the jaw members and the inter-engagement between the cam and follower surfaces of the jaw members and the male coupling, respectively.

23. A coupling system as defined in claim 21, wherein said jaw members and said wedge members each include wedge surfaces which are substantially complementary in curvature to the spherical outer surface of said ball to provide lenticular type surface contact between said ball and said jaw members and wedge members due to elastic deformation.

24. A coupling system as defined in claim 21, wherein said female coupling has outer sidewalls including opposing openings for receiving said wedge members during the assembly of said system, and for affording access to said screw member.

25. A coupling system as defined in claim 24, wherein one of said sidewall openings provides a passageway for the installation of said ball between said jaw members during the assembly of the coupling system.

26. A coupling system for lockably coupling together machine tool components, comprising:
  (a) a female coupling having:
    (i) a body having an axis,
    (ii) an opening disposed along said axis for receiving the distal end of a male coupling and having walls,
    (iii) a plurality of lugs within said opening extending from said walls, and
    (iv) a plurality of opposing jaw members movably mounted in said opening, having feet which engage said lugs to limit axial travel of said members and said jaw members further having cam surfaces for engaging follower surfaces of a male coupling and urging said surfaces both radially outwardly from said axis and longitudinally along said axis when said jaw members are moved apart orthogonally with respect to said axis, and
  (b) a drive train for moving said jaw members apart and for securing the male coupling, including
    (i) an axially movable drive element for driving said jaw members apart,
    (ii) a pair of opposing wedge members orthogonally movable with respect to said axis for moving said drive element axially, and
    (iii) a member for driving said wedge members orthogonally toward and away from one another.

27. A coupling system as defined in claim 26, wherein said wedge members further wedgingly engage and drive apart a second coupling from the opening of the first coupling when said member drives the wedge members orthogonally away from one another.

28. A coupling system as defined in claim 26, wherein the angle of wedging contact between the drive element and the jaw members is such that the distance that each of the jaw members moves orthogonally with respect to said axis is less than the axial distance travelled by the drive element whereby a mechanical advantage is obtained between the drive element and the jaw members.

29. A coupling system as defined in claim 26, wherein the angle of wedging contact between the wedge members and the drive element is such that the distance that each of the wedge elements moves orthogonally is greater than the distance that the drive element travels axially whereby a mechanical advantage is obtained between the pair of wedge members and the drive element.

30. A coupling system as defined in claim 26, wherein the jaw members are pivotally mounted on one end to the first coupling, and the drive element engages the jaw members at a point on an opposite end of each which is further away from said one end of each than said cam surfaces to provide a mechanical advantage between the action of the drive element driving apart the jaw members and the inter-engagement between the cam surfaces of the jaw members and said follower surfaces, respectively.

* * * * *